(12) United States Patent
Wang et al.

(10) Patent No.: US 10,335,293 B2
(45) Date of Patent: Jul. 2, 2019

(54) DAMPING CONTROL METHOD FOR LOWER-LIMB PROSTHESES

(71) Applicant: PEKING UNIVERSITY, Beijing (CN)

(72) Inventors: Qining Wang, Beijing (CN); Kebin Yuan, Beijing (CN); Jinying Zhu, Beijing (CN); Long Wang, Beijing (CN)

(73) Assignee: PEKING UNIVERSITY, Shenzhen (CN)

( * ) Notice: Subject to any disclaimer, the term of this patent is extended or adjusted under 35 U.S.C. 154(b) by 96 days.

(21) Appl. No.: 15/023,996

(22) PCT Filed: Oct. 21, 2014

(86) PCT No.: PCT/CN2014/000936
§ 371 (c)(1),
(2) Date: Mar. 22, 2016

(87) PCT Pub. No.: WO2016/041100
PCT Pub. Date: Mar. 24, 2016

(65) Prior Publication Data
US 2018/0177614 A1    Jun. 28, 2018

(30) Foreign Application Priority Data
Sep. 18, 2014    (CN) .......................... 2014 1 0479753

(51) Int. Cl.
*A61F 2/70*        (2006.01)
*A61F 2/66*        (2006.01)
(Continued)

(52) U.S. Cl.
CPC .............. *A61F 2/6607* (2013.01); *A61F 2/60* (2013.01); *A61F 2/70* (2013.01);
(Continued)

(58) Field of Classification Search
None
See application file for complete search history.

(56) References Cited

U.S. PATENT DOCUMENTS

| 7,652,386 B2 * | 1/2010 | Donelan | .................. F03G 5/00 290/1 R |
|---|---|---|---|
| 2009/0192619 A1 * | 7/2009 | Martin | ..................... A61F 2/60 623/18.11 |
| 2013/0317626 A1 | 11/2013 | Loverich et al. | |

FOREIGN PATENT DOCUMENTS

| CN | 101856283 A | 10/2010 |
|---|---|---|
| CN | 101961271 A | 2/2011 |

(Continued)

OTHER PUBLICATIONS

Yang, P. et al., "Intelligent Prosthetic Ankle Based on the Finite State Machine Control," Chinese Journal of Tissue Engineering Research, vol. 17, No. 9, Feb. 26, 2013, 8 pages.

*Primary Examiner* — David H Willse
(74) *Attorney, Agent, or Firm* — McCoy Russell LLP

(57) ABSTRACT

A damping control method for a lower-limb prosthesis, comprising the following steps: isolate the driving motor of the lower-limb prosthesis from the driving voltage; the driving motor is driven to rotate by the force that results from locomotion of a human's CoM (Center of Mass), and generates an alternating induced voltage, when the driving motor behaves as a generator; connect output terminals of the driving motor with a full-bridge rectification circuit that is made of Schottky diodes to transform the alternating induced voltage to a direct-current voltage; connect the output terminals of the full-bridge rectification circuit with a controlled switch to form a closed circuit, which will generate induced current from the induced voltage; control the on-off ratio of the controlled switch with a Pulse-Width-Modulation signal to generate a controllable motor current, (Continued)

which will result in controllable braking torque under the magnet field of the driving motor.

8 Claims, 1 Drawing Sheet

(51) Int. Cl.
*A61F 2/60* (2006.01)
*A61F 2/50* (2006.01)
*A61F 2/68* (2006.01)

(52) U.S. Cl.
CPC ............. *A61F 2002/5006* (2013.01); *A61F 2002/5033* (2013.01); *A61F 2002/607* (2013.01); *A61F 2002/6818* (2013.01); *A61F 2002/701* (2013.01); *A61F 2002/704* (2013.01); *A61F 2002/708* (2013.01)

(56) References Cited

FOREIGN PATENT DOCUMENTS

| CN | 102202613 A | 9/2011 |
| CN | 101785716 B | 6/2012 |
| WO | 2014005709 A2 | 1/2014 |

* cited by examiner

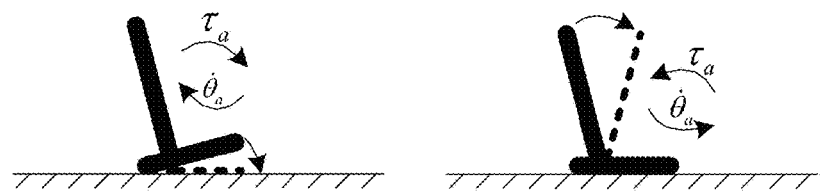
Fig. 1A          Fig. 1B
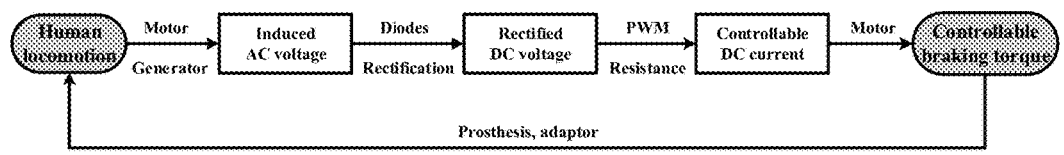
Fig. 2
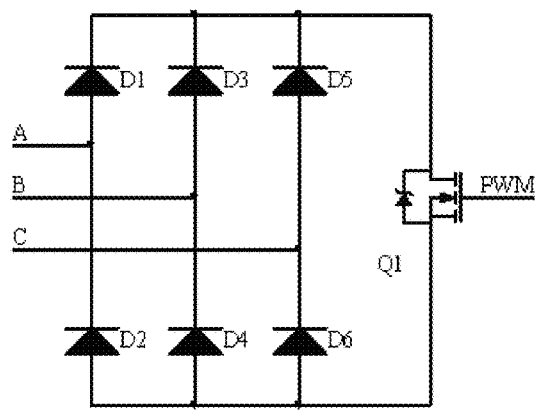
Fig. 3

DAMPING CONTROL METHOD FOR LOWER-LIMB PROSTHESES

CROSS REFERENCE TO RELATED APPLICATIONS

The present application is a U.S. National Phase of International Patent Application Serial No. PCT/CN2014/000936, entitled "A DAMPING CONTROL METHOD FOR LOWER-LIMB PROSTHESES," filed on Oct. 21, 2014, which claims priority to Chinese Patent Application No. 201410479753.5, entitled "A DAMPING CONTROL METHOD FOR LOWER-LIMB PROSTHESES," filed on Sep. 18, 2014, the entire contents of each of which are hereby incorporated by reference for all purposes.

FIELD OF THE INVENTION

The invention relates to a damping control method, and more particularly, to a damping control method for lower-limb prosthesis.

BACKGROUND OF THE INVENTION

According to the statistics of China Disabled Persons' Federation in 2012, China has more than 20,000,000 amputees. Limb loss has brought them lots of inconveniences to their daily living and deteriorate their life quality. Lower-limb prostheses help the transtibial amputees restore their ability to stand and walk, and can significantly improve their life quality. Currently the commercial transtibial prostheses can be classified into two categories according to the ankle angle adjustment ability: the fixed-ankle prostheses and the adjustable-ankle prostheses. Fixed-ankle prostheses can help the wearer to support their body, but cannot mimic the dynamic characteristics of the normal ankle. Adjustable-ankle prostheses can adjust the ankle angle within a pre-defined range as the normal ankle, but their ankle impedance is usually determined by the mechanical structure and prosthesis material, and cannot be adjusted according to different walking speeds and terrains. Consequently, amputees may suffer from asymmetric gait patterns and decreased walking stabilities when walking on ramps and stairs with these kinds of prostheses.

To deal with speed and terrain variations, the ankle should be able to modulate the joint impedance. Patent CN101785716B has presented a hydraulic bionic ankle prosthesis, which controls the opening size of the oil fluid tube with a throttle valve, and consequently controls the flow resistance of the fluid and the joint rotation impedance. Patent CN101856283B has presented a pneumatic ankle prosthesis, which controls the opening size of an air cylinder with a stepping motor to control the joint impedance. Both the hydraulic and pneumatic prostheses above can control the ankle impedance, but it requires adding damping control components in addition to the main mechanical structure, which makes the prosthesis design more complicated. Moreover, there are risks of fluid or air leakage for these kinds of designs during long time operation.

SUMMARY OF THE INVENTION

To overcome the above drawbacks, the invention presents a new damping control method for lower-limb prostheses, which has simple structure, high stability, and requires no additional components.

To achieve the above objectives, the invention is realized with the following technical schemes. A damping control method for lower-limb prosthesis, which is characterized by: (1) Isolate the motor from the driving voltage, and make the motor to function as a generator; (2) The generator generates induced voltage from the joint rotation that resulted from the locomotion of human's CoM (Center of Mass); (3) Transform the alternating induced voltage to direct-current voltage with a full-bridge rectification circuit made of Schottky diodes; The Schottky diodes can also be replaced by the "ideal" diodes made of MOSFETs to decrease the voltage drop; (4) Connect the output terminals of the rectification circuit with a controlled switch such as transistors or MOSFETs to form a closed circuit, and generates induced current from the induced voltage; (5) Control the on-off ratio of the switch with the Pulse-Width-Modulation (PWM) signal to generate controllable motor current, which will result in controllable braking torque under the magnet field of the motor.

In step (3), the MOSFET is preferred to be connected with the output terminal of the full-bridge rectification circuit.

The full-bridge rectification circuit is made of six diodes. The inputs of the rectification circuit is the induced alternating voltage from the three phases of the motor (A, B, C). The positive output of the rectification circuit is connected with the drain terminal of the MOSFET, while the negative output is connected with the source terminal of the MOSFET. The PWM control signal is connected with the gate terminal of the MOSFET.

Thanks to the technical schemes described above, the invention has several advantages:
1. The invention generates damping with different kinds of small-size electronic components such as transistors, MOSFETs, and diodes from the motor rotation, and requires no additional mechanical components, which simplifies the mechanical design of the prosthesis.
2. The invention controls the damping with the Pulse-Width-Modulation (PWM) signal, which has better precision and is easier to implement than controlling a throttle valve with stepping motors.
3. The invention generates damping from the energy of human locomotion instead of external energy source such as a battery, which makes the invention quite energy efficient.

BRIEF DESCRIPTION OF THE FIGURES

The accompanying drawings are included to provide a further understanding of the invention. The drawings illustrate embodiments of the invention and, together with the description, serve to explain the principles of the invention.

FIGS. 1A and 1B show the angular speed and joint torque of the ankle during walking. FIG. 1A refers to the controlled plantarflexion, and FIG. 1B refers to the controlled dorsiflexion.

FIG. 2 shows the overall implementation process of the invented damping control method from human locomotion to the controllable braking torque.

FIG. 3 shows the schematic diagram of the rectification circuit which consists of 6 diodes, and the PWM control circuit which mainly consists of one or multiple MOSFETs in parallel.

DESCRIPTION OF THE DETAILED IMPLEMENTATION

The implementation process of the proposed invention will be described in detail in the following session.

One gait cycle of human locomotion can be divided into different gait phases. According to whether the foot is on the ground or not, the gait cycle can be divided into stance phase when the foot is on the ground, and swing phase when the foot is off the ground. This invention mainly concentrates on the period from heel-strike to the moment when the ankle reaches the maximal dorsiflexion. This period is essential for terrain adaptation, when the ankle is driven to rotate by the external force from human locomotion. The detailed implementation process is shown in FIG. 2, which includes the following steps:

Isolate the driving motor of the main transmission structure from the driving voltage, and make the motor to function as a generator;

The generator generates induced voltage from the joint rotation that resulted from the locomotion of human's CoM (Center of Mass);

Transform the alternating induced voltage to direct-current voltage with a full-bridge rectification circuit made of Schottky diodes; The Schottky diodes can also be replaced by the "ideal" diodes that are made of MOSFETs to decrease the voltage drop;

Connect the output terminals of the rectification circuit with a controlled switch such as transistors or MOSFETs to form a closed circuit, and generates induced current from the induced voltage;

Control the on-off ratio of the switch with the Pulse-Width-Modulation (PWM) signal to generate controllable motor current, which will result in controllable braking torque under the magnet field of the motor.

The rectification circuit of step 3) is mainly made of six diodes (D1~D6) shown in FIG. 3. The inputs of the rectification circuit is the induced alternating voltage from the three phases of the motor (A, B, C), and the output is connected to the Drain terminal of the MOSFET (Q1), which behaves as a controlled switch that is controlled by the external PWM signal at the Gate terminal.

In summary, from the moment of heel-strike to the moment when the ankle reaches the maximal dorsiflexion angle, the ankle joint is driven to rotate passively and behaves as a generator. Rotation of the generator generates induced voltage, which is firstly rectified by the rectification circuit, and then transformed to controllable induced current by a controlled switch made of MOSFETs. The induced current will generate braking torque that prevents the ankle from rotating, thus enable a smooth locomotion of the body CoM.

The embodiments that have been described above are merely illustrative of and not restrictive on the broad invention. It will be understood to those skilled in the art that various modifications can be made to the structure, operation method and manufacture of the invention without departing from the scope or spirit of the invention. Accordingly, the invention covers the modifications and variations of this invention that fall within the scope of the claims.

The invention claimed is:

1. A damping control method for a lower-limb prosthesis, comprising the following steps:
    isolating a driving motor of the lower-limb prosthesis from a driving voltage, and operating the driving motor as a generator,
    wherein the generator generates an alternating induced voltage from a joint rotation resulting from locomotion of a human body's CoM (Center of Mass), and where the method further comprises:
        transforming the alternating induced voltage to a direct-current voltage with a full-bridge rectification circuit made of Schottky diodes or ideal diodes;
        connecting output terminals of the full-bridge rectification circuit with a controlled switch to form a closed circuit, and generating induced current from the direct-current voltage; and
        controlling the on-off ratio of the controlled switch with a Pulse-Width-Modulation (PWM) signal to generate a controllable motor current that results in a controllable braking torque under the magnetic field of the driving motor.

2. The method of claim 1, wherein the controlled switch connected to the output terminals of the full-bridge rectification circuit comprises a metal oxide semiconductor field effect transistor (MOSFET).

3. The method of claim 2, wherein:
    the full-bridge rectification circuit is made of several Schottky diodes,
    wherein input of the full-bridge rectification circuit is connected to terminals of three phases of the driving motor,
    wherein the positive output of the full-bridge rectification circuit is connected to the drain terminal of the MOSFET,
    wherein the negative output of the rectification circuit is connected to the source terminal of the MOSFET, and
    wherein the PWM signal is connected to the gate terminal of the MOSFET.

4. The method of claim 3, wherein the several of the Schottky diodes further comprises four Schottky diodes where the driving motor comprises a brushed direct current motor; and
    wherein the several of the Schottky diodes further comprises six Schottky diodes where the driving motor comprises a brushless direct current motor.

5. The method of claim 1, wherein the diodes are Schottky diodes.

6. The method of claim 1, wherein the diodes are ideal diodes comprised of MOSFETs to decrease the voltage drop across the diodes.

7. The method of claim 1, wherein the controlled switch comprises one or more transistors.

8. The method of claim 1, wherein the damping control method relates to a period from when a heel of a foot of a human body strikes ground to when an ankle of the foot reaches a maximal dorsiflexion.

* * * * *